(12) United States Patent
Bohn et al.

(10) Patent No.: US 7,899,535 B2
(45) Date of Patent: Mar. 1, 2011

(54) AUTOMATIC ELECTRODE INTEGRITY MANAGEMENT SYSTEMS AND METHODS

(75) Inventors: Derek D. Bohn, Woodbury, MN (US); M. Jason Brooke, Minneapolis, MN (US); Rajesh Krishan Gandhi, Woodbury, MN (US); Alok S. Sathaye, Minneapolis, MN (US); Aaron McCabe, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1290 days.

(21) Appl. No.: 11/424,579

(22) Filed: Jun. 16, 2006

(65) Prior Publication Data

US 2007/0293903 A1 Dec. 20, 2007

(51) Int. Cl.
*A61N 1/08* (2006.01)
(52) U.S. Cl. ............................................ 607/27; 607/28
(58) Field of Classification Search .................. 607/27, 607/28
See application file for complete search history.

(56) References Cited

U.S. PATENT DOCUMENTS

| 4,899,750 | A | 2/1990 | Ekwall |
| 5,453,698 | A | 9/1995 | Williams et al. |
| 5,549,646 | A | 8/1996 | Katz et al. |
| 5,755,742 | A | 5/1998 | Schuelke et al. |
| 5,944,746 | A | 8/1999 | Kroll |
| 6,104,954 | A | 8/2000 | Blunsden |
| 7,047,083 | B2 | 5/2006 | Gunderson et al. |
| 7,058,449 | B2 | 6/2006 | Stahmann et al. |
| 7,120,493 | B2 | 10/2006 | Propp et al. |
| 2003/0004552 | A1* | 1/2003 | Plombon et al. ............. 607/27 |
| 2005/0049644 | A1 | 3/2005 | Warren et al. |
| 2005/0137636 | A1 | 6/2005 | Gunderson et al. |
| 2007/0066998 | A1* | 3/2007 | Hansen et al. ................ 607/4 |

FOREIGN PATENT DOCUMENTS

| WO | WO-9819738 A1 | 5/1998 |
| WO | WO-9924113 A1 | 5/1999 |
| WO | WO-0043065 A1 | 7/2000 |
| WO | WO-0218009 A1 | 3/2002 |
| WO | WO-2004011090 A3 | 2/2004 |
| WO | WO-2004028617 A2 | 4/2004 |
| WO | WO-2004028617 A3 | 4/2004 |

OTHER PUBLICATIONS

Dilling-Boer, Dagmara, et al., "Occurrence of ICD Lead Fracture is Related to Foregoing ICD Replacement or Lead Intervention", *Heart Rhythm*, vol. 1, Issue 1, Supplement 1, (2004), S208-S209.
Hauser, Robert G., et al., "Clinical features and management of atrial and ventricular pacing lead failure: A multicenter registry study", *Heart Rhythm*, vol. 1, Issue 1, Supplement 1, (2004), S13.
Hauser, Robert G., et al., "The multicenter registry's experience with 4,059 ICD and pacemaker pulse generator and lead failures", *Heart Rhythm*, vol. 2, Issue 5, Supplement 1, (May 2005), S30.

* cited by examiner

*Primary Examiner* — Eric D. Bertram
(74) *Attorney, Agent, or Firm* — Schwegman, Lundberg & Woessner, P.A.

(57) ABSTRACT

This document discusses, among other things, systems and methods for automatic electrode integrity management. Inter-electrode impedance is measured for various electrode combinations of an implantable cardiac function management device. The impedance data is processed, such as at an external remote server, to determine whether an electrode is failing or has failed, to select an alternate electrode configuration, to alert a physician or patient, to predict a time-to-failure such as by using population data, or to reprogram electrode configuration or other device parameters of the implantable cardiac function management device.

19 Claims, 6 Drawing Sheets

AUTOMATIC ELECTRODE INTEGRITY MANAGEMENT SYSTEMS AND METHODS

TECHNICAL FIELD

This patent document pertains generally to managing implantable medical devices and more particularly, but not by way of limitation, to automatic lead integrity management systems and methods.

BACKGROUND

Implantable medical devices include cardiac function management devices, such as pacers, cardioverters, defibrillators, cardiac resynchronization therapy devices, or devices having a combination of such attributes. Such devices generally use electrodes, such as for sensing intrinsic electrical heart signals, for delivering stimulations to induce heart contractions, or for delivering a countershock ("shock") to interrupt a tachyarrhythmia. Such electrodes may include, for example: an intracardiac electrode located within a heart (e.g., on a multiconductor or other intravascular lead); an epicardial electrode located on the heart; or a can or header or other electrode located at or near an electronics unit, which is generally implanted pectorally, abdominally, or elsewhere.

Mechanical stress may affect an intravascular intracardiac lead, having multiple such intracardiac electrodes located at or near its distal end, with multiple conductors leading to a connector at its proximal end, which connects to an implantable electronics unit of a cardiac function management system. Lead failures are a well established problem for the medical device industry. For example, an implantable cardioverter-defibrillator (ICD) lead failure rate of 2.73% at 56 months ±28 months has been reported. See Dagrnara, et al., *Occurrence of ICD Lead Fracture Is Related to Foregoing ICD Replacement or Lead Intervention*, Heart Rhythm, 2001. 1(1): p. S208-S209. Another example reported a mean time to failure of 6.8+/−5 years for ventricular pacing leads and 6.0+/−4.2 years for atrial pacing leads. See Hauser et al., *Clinical Features and Management of Atrial and Ventricular Pacing Lead Failure: A Multicenter Registry Study*, Heart Rhythm, 2004. 1(1): p. S13. Lead failures may take several different forms, or failure modes. One example of ICD lead failures were classified as: 43% lead insulation failures, 31% low voltage (e.g., pacing electrode) conductor failures, and 10% high voltage (e.g., shock electrode) conductor failures. See Hauser et al., *The Multicenter Registry's Experience with 4,059 ICD and Pacemaker Pulse Generator and Lead Failures*, Heart Rhythm, 2005, 2(5): p. S30. Lead failures can result in an apparent short circuit between electrodes, or in an open circuit to one or more electrodes for sensing or delivering electrical energy. This can adversely affect performance of the accompanying cardiac function management system. For example, for a tachyarrhythmia patient with an ICD, a lead failure may result in the ICD inappropriately sensing mere noise as tachyarrhythmic cardiac depolarizations, resulting in unwarranted delivery of a shock. As another example, for a bradycardia patient with a pacer, a lead failure may result in loss of pacing, resulting in inadequate cardiac output for the patient. In sum, lead failures can have serious consequences for patients with cardiac function management devices.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
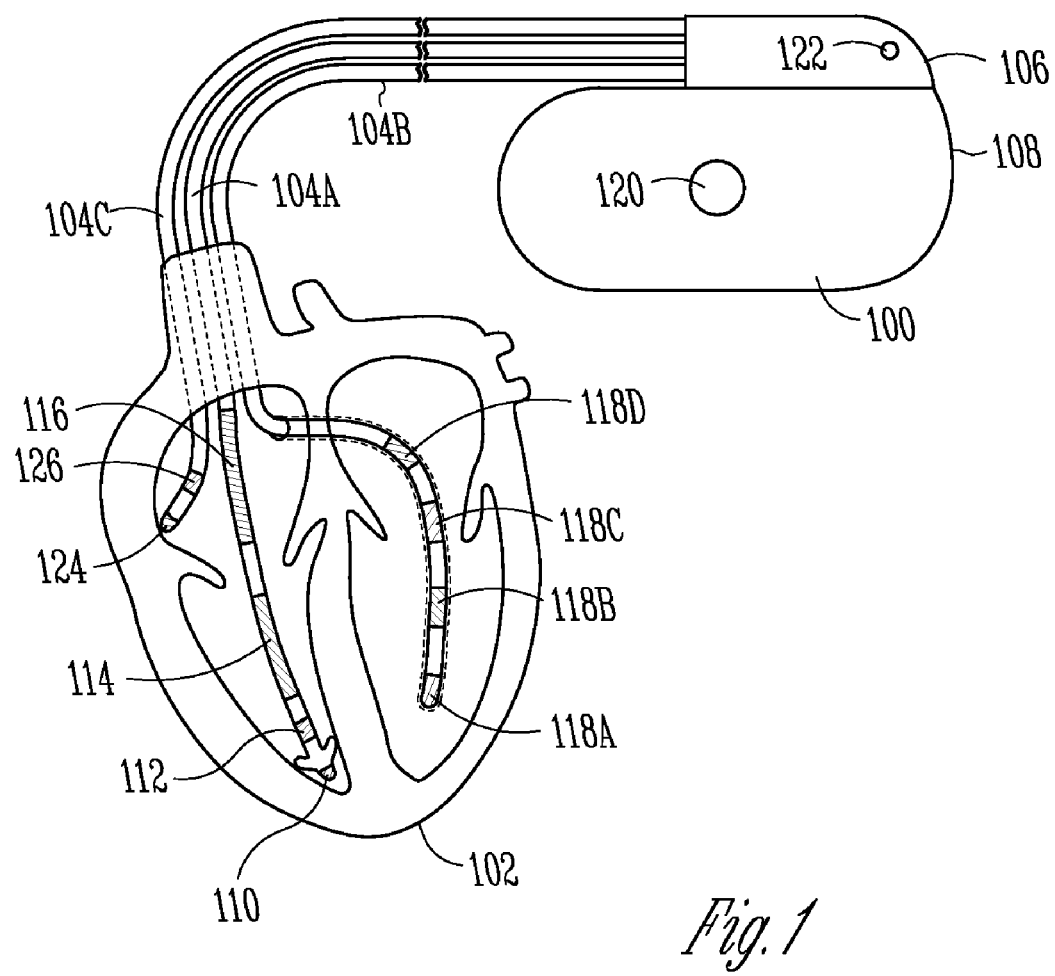
FIG. 1 is a schematic drawing illustrating generally one example of an implantable cardiac function management device that is coupled to a heart using one or more intravascular leads.

FIG. 1 is a schematic drawing illustrating generally one example of an implantable cardiac function management device 100 that is coupled to a heart 102 using one or more intravascular leads 104. In this illustrative example, a lead 104A has its proximal end connected to a header 106 portion of the device 100, with the header 106, in turn, connected to a hermetically sealed electronics unit 108. In this illustrative example, the distal portion of multi-conductor lead 104A extends into a right ventricle of the heart 102, and includes a tip electrode 110, a ring electrode 112, a distal shock electrode 114 and a proximal shock electrode 116. This example also shows a lead 104B that has its proximal end connected to the header 106. The distal portion of the lead 104B extends into a coronary sinus or great cardiac vein, and provides four electrodes 118A-D located near the left ventricle of the heart 102. Other leads may extend elsewhere, such as lead 104C extending into the right atrium, for example, to provide a distal tip electrode 124 and a slightly more proximal ring electrode 126. The electronics unit 108 of the device 100 may also include electrodes, such as a can electrode 120 or a header electrode 122, or one or more other electrodes located at the device 100 or nearby, or one or more epicardial electrodes, or any other suitable configuration of electrodes. Such electrodes may be individually connected back to the device 100 or, in certain circumstances, may share one or more common conductors back to the device 100.

Figure 2:
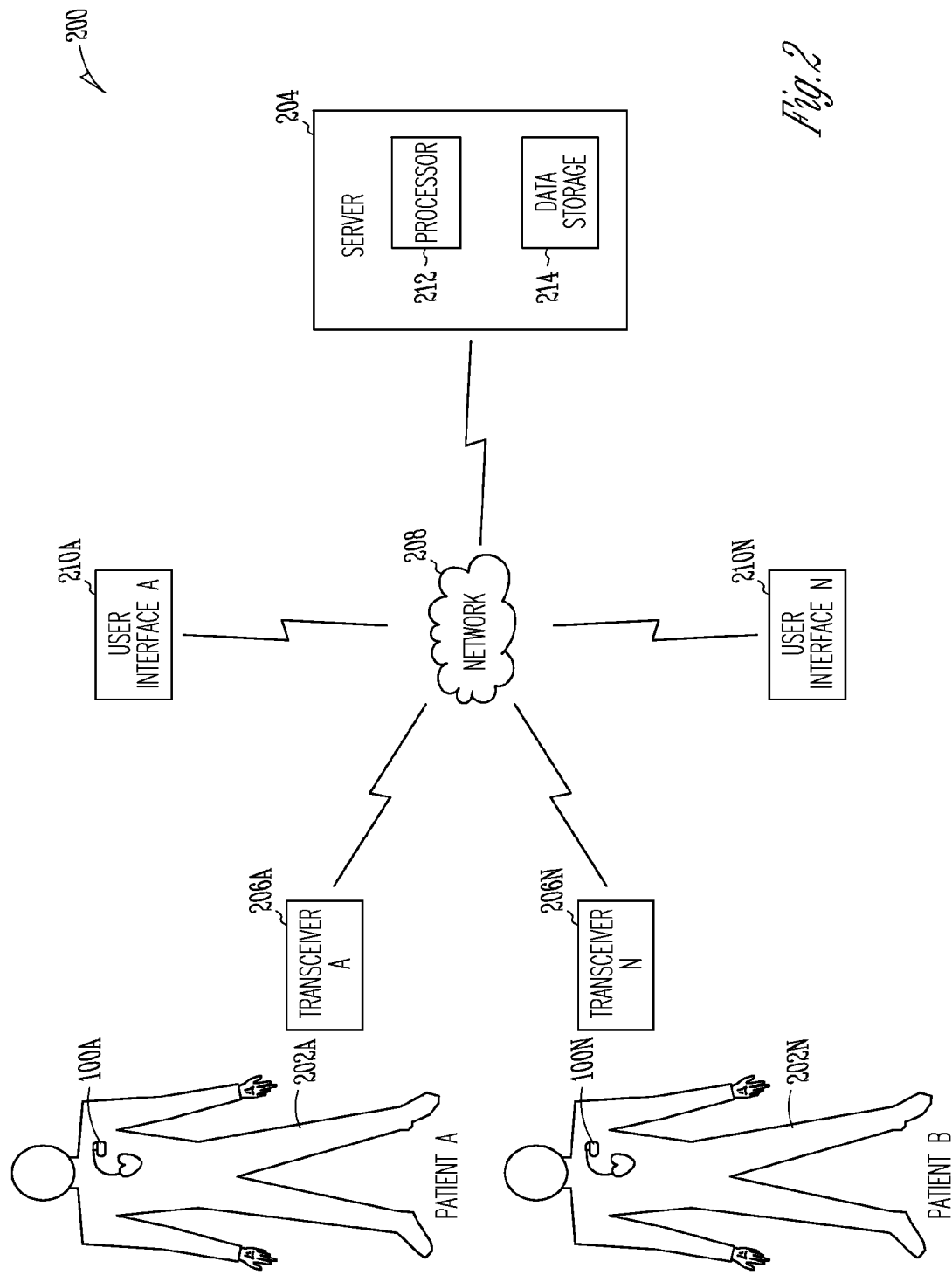
FIG. 2 is a schematic drawing illustrating generally an example of a distributed patient management system for managing multiple implantable devices, which are generally, but not necessarily, located in different patients.

FIG. 2 is a schematic drawing illustrating generally an example of a distributed patient management system 200 for managing multiple implantable devices 100A-N, which are generally, but not necessarily, located in different patients 202A-N. Each implantable device 100 communicates with a server 204, which can be remote from one or all of the patients 202. The example of FIG. 2 shows intermediary transceivers 206A-N for each of the implantable devices 202A-N, however, this is not necessary. For example, the transceiver 206A communicates wirelessly with the implanted device 100A, such as by a radio frequency (RF) link, an inductive link, or otherwise. The transceiver 206A also provides wired or RF or other wireless communication with the server 204, such as through a telecommunications or computer network 208. In this example, the patient management system 200 includes one or more computer or other user interfaces 210A-N, which communicate with the server 204 over the network 208, such as via a wired or wireless link. Such a user interface 210 permits a physician or other user to connect to the server 204, such as for interacting with one or more of the implantable cardiac function management devices 100A-N. This may include reviewing or using physiological data or device settings communicated from an implantable cardiac function management device 100 to the server 204, or even for remotely programming an implantable cardiac rhythm management device 100. The server 204 generally includes a processor 212 and data storage 214 to help the user analyze cardiac function management device status, settings, and physiological data.

Figure 3:
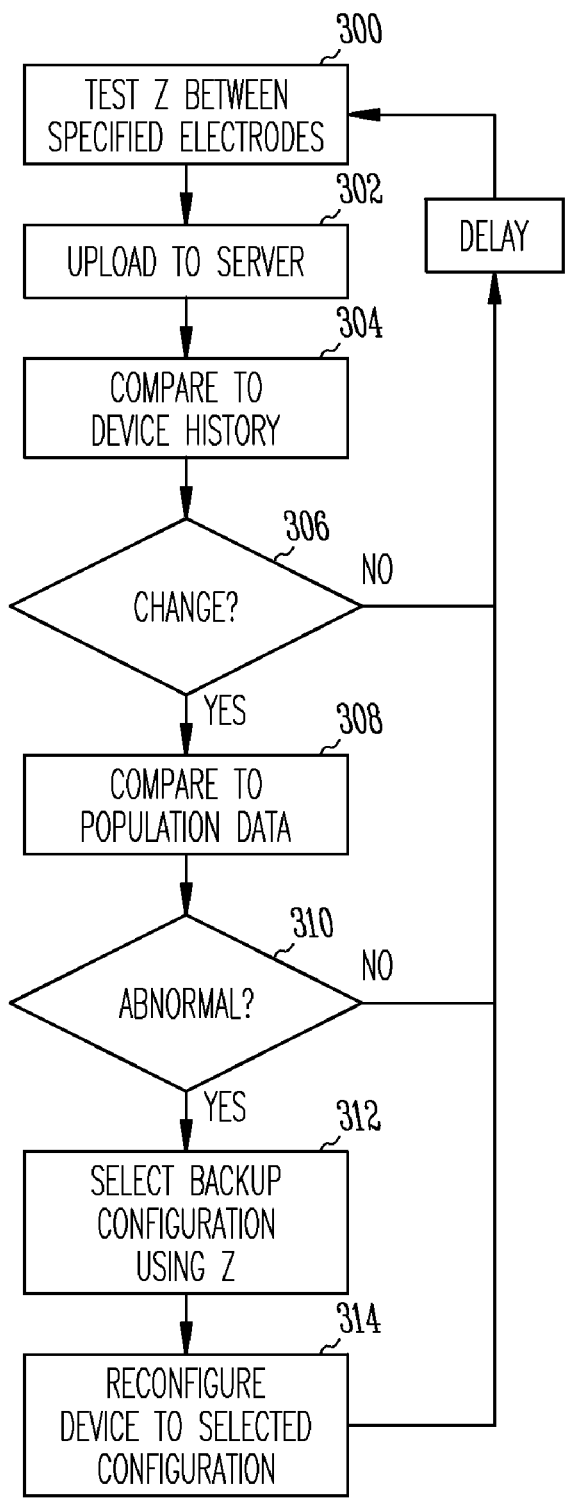
FIG. 3 is a flow chart illustrating generally an example of using a server for managing the electrode configuration of various implantable cardiac function management devices, such as for ensuring the integrity and proper functioning of such electrodes by monitoring electrode impedance.

FIG. 3 is a flow chart illustrating generally an example of using the server 204 for managing the electrode configuration of various implantable cardiac function management devices 100A-N, such as for ensuring the integrity and proper functioning of such electrodes by monitoring electrode impedance. Although FIG. 3 focuses on the interaction between the server 204 and a particular cardiac function management device 100A, the server 204 will generally interact with multiple such cardiac function management devices 100A-N, which are generally respectively implanted in different patients, although a single patient could have multiple devices 100.

In the example of FIG. 3, at 300, an implantable cardiac function management device 100A tests interelectrode impedance for various specified combinations of two or more electrodes. An exemplary illustrative list specifying combinations of electrodes for which impedance is to be tested is given in Table 1, which is provided by way of example only, and not by way of limitation.

TABLE 1

Example of electrode combinations for testing impedance between first electrode(s) and second electrode(s)

| First Electrode(s) | Second Electrode(s) |
|---|---|
| RV tip electrode 110 | RV ring electrode 112 |
| RA tip electrode 124 | RA ring electrode 126 |
| LV electrode 118A | LV electrode 118B |
| RV shock electrode 114 | SV shock electrode 116 |
| RV tip electrode 110 | Can electrode 120 |
| RA tip electrode 124 | Can electrode 120 |
| LV electrode 118A | Can electrode 120 |
| RV shock electrode 114 | Can electrode 120 |
| RV ring electrode 112 | Can electrode 120 |
| RA ring electrode 126 | Can electrode 120 |
| LV electrode 118B | Can electrode 120 |
| SV shock 116 | Can electrode 120 |
| Etc. | Etc. |

In certain examples, the impedance will be tested between combinations of multiple electrodes, such as between (1) electrodes 118A and 118B (in common with each other) and (2) electrodes 118C and 118D (in combination with each other). Moreover, certain electrodes may appear in more than one combination. For example, an electrode that appears in a failed or failing electrode combination may nonetheless also appear in one or more of the backup electrode combinations being tested, and may appear either alone, or in combination with one or more other electrodes.

In certain examples, an indication of interelectrode impedance is measured by delivering a specified fixed amplitude (e.g., typically biphasic) test current pulse between one or more commonly connected first electrodes and one or more commonly connected second electrodes, and measuring the resulting voltage between the first and second electrode(s). The impedance is given by the measured voltage divided by the specified current, and the actual impedance need not be calculated since the resulting voltage gives a signal that is proportional to, and therefore indicative of, the interelectrode impedance. The delivered test current is optionally subthreshold in amplitude and frequency (e.g., 80 microamperes, 78 microsecond per phase of a four-phase biphasic pulse train), such that it does not evoke a resulting heart contraction. The test current can be generated, in certain examples, using a circuit that is also used for performing thoracic impedance measurements, such as for performing minute ventilation (MV) regulation of pacing rate. In other examples, the impedance measurement is made using, as a test energy or excitation energy, the energy delivered during a pacing pulse. In certain examples, the test current can be delivered at a single electrode, and received by multiple electrodes. In certain other examples, the test current can be delivered at multiple electrodes and received by multiple other electrodes. In certain further examples, the test current can be delivered at multiple electrodes and received by a single electrode. A list of candidate electrode combinations to be tested is typically used to operate a multiplexer in the electronics unit 108 to connect to the desired electrodes for performing the desired impedance measurements. The interelectrode impedance testing at 300 is typically performed recurrently, such as periodically with a specified frequency.

At 302, after the interelectrode impedance data has been collected for all the electrode combinations specified on a list, such as the list shown in Table 1, or a pre-specified subset thereof, then the resulting impedance data is uploaded to the server 204 and stored in the data storage 214, such as in a record associated with the particular implantable cardiac function management device 100A from which it was obtained. The uploading at 302 is typically performed recurrently, such as periodically with a specified frequency, which may be different from the frequency of testing interelectrode impedance at 300. Thus, at 302, the data uploaded may include interelectrode impedance test data acquired over a period of time between uploading events. In certain examples, the uploading at 302 is initiated by the server 204, which "polls" the implantable cardiac function management devices 100. In other examples, the uploading at 302 is initiated by the particular implantable cardiac function management device 100, which "pushes" data out to the server 204.

At 304, the interelectrode impedance data is compared to a history of such data previously obtained from the same implantable cardiac function management device 100. This generally involves comparing data from each tested electrode configuration to previously obtained data for the same electrode configuration, such as to determine whether there has been a statistically significant change. This may involve comparing the most recent data (or a short term average or the like) to earlier or longer term data (such as an initial measurement, a long term average, or the like).

At 306, if such a change in interelectrode impedance has been detected, then at 308 the changed interelectrode impedance data is optionally compared to patient or population data. Patient data includes other data previously obtained from the same patient. Such a comparison helps determine whether the observed change in interelectrode impedance in a particular patient is significant with respect to previously observed measurement or trend data such that it represents an actual or impending failure. If no patient data is yet available (e.g., for a newly implanted lead), then predictive laboratory or simulation modeled data or other data can be used for performing this comparison. Population data generally includes interelectrode impedance data from a like electrode configuration used by other implantable cardiac function management devices, e.g., 100B-N, that use the same type (e.g., model) of lead. Such a comparison helps determine whether the observed not-insignificant change in interelectrode impedance in a particular patient represents an actual or impending failure already being observed in other patients. If no population data is yet available (e.g., for a new lead model), then predictive laboratory or simulation modeled data or other data can be used for performing this comparison.

In making the comparison at 308 to population data, it may be desirable to normalize the interelectrode impedance data, such as to initial or earlier data obtained from the same patient, such that it is a change in interelectrode impedance for a particular patient that is being compared to corresponding changes in interelectrode impedance for the same electrode configuration as observed in other patients in the population. In certain examples, it is a trend over time of such normalized values from a particular patient that is compared to one or more trends over time of such normalized values from other patients in the population.

Since various patients in the population may have experienced different lead failure modes, in certain examples, the population data is analyzed such that data from patients deemed to exhibit the same failure mode are used together, such as in a composite trend over time for that particular failure mode. Data from a particular patient can be compared to multiple such composite trends to determine whether the patient is exhibiting the signs of a particular failure mode. The ability to separately represent and test for different failure modes separately may increase the predictive capability of the present techniques. Since interelectrode impedance data is generally obtained and uploaded for all possible electrode configurations, a failed or failing electrode can be positively identified by comparing interelectrode impedance data for the various electrode combinations, and may not even require testing all such electrode configurations in order to make such a positive identification.

At 310, if the comparison at 308 indicates an abnormal interelectrode impedance for a particular electrode configuration, and that particular electrode configuration is being used by the implantable cardiac function management device 100A for sensing or delivering electrical energy, then at 312 an alternative electrode configuration can be selected. In certain examples, the particular electrode configuration having an abnormal impedance reading has a list of backup electrode configurations that can be substituted for sensing or delivering electrical energy. In certain examples, a particular backup electrode configuration is selected by comparing interelectrode impedance data for such alternative backup electrode configurations, and selecting a particular backup electrode configuration using the comparison. In other examples, the list of backup electrode configurations is ordered, for example, by similarity of locations of the electrodes in the backup electrode configuration to the locations of the electrode configuration for which it is being substituted, and the impedance data is only used to choose between backup electrode configurations that are similarly located.

At 314, after a failed or failing electrode configuration has been identified at 310, and the most suitable backup electrode configuration has been selected at 312, then, at 314, the particular implantable cardiac function management device 100A is automatically reprogrammed to the selected backup electrode configuration, and an alert notifying of the same is automatically generated and communicated to one or more of the patient, the patient's physician, the manufacturer of the cardiac function management device 100A, or the manufacturer of the lead being used by the cardiac function management device 100A. After 314, a "No Change" determination at 306, or a "Not Abnormal" determination at 310, process flow then returns to 300, after an optional delay 316.

Figure 4:
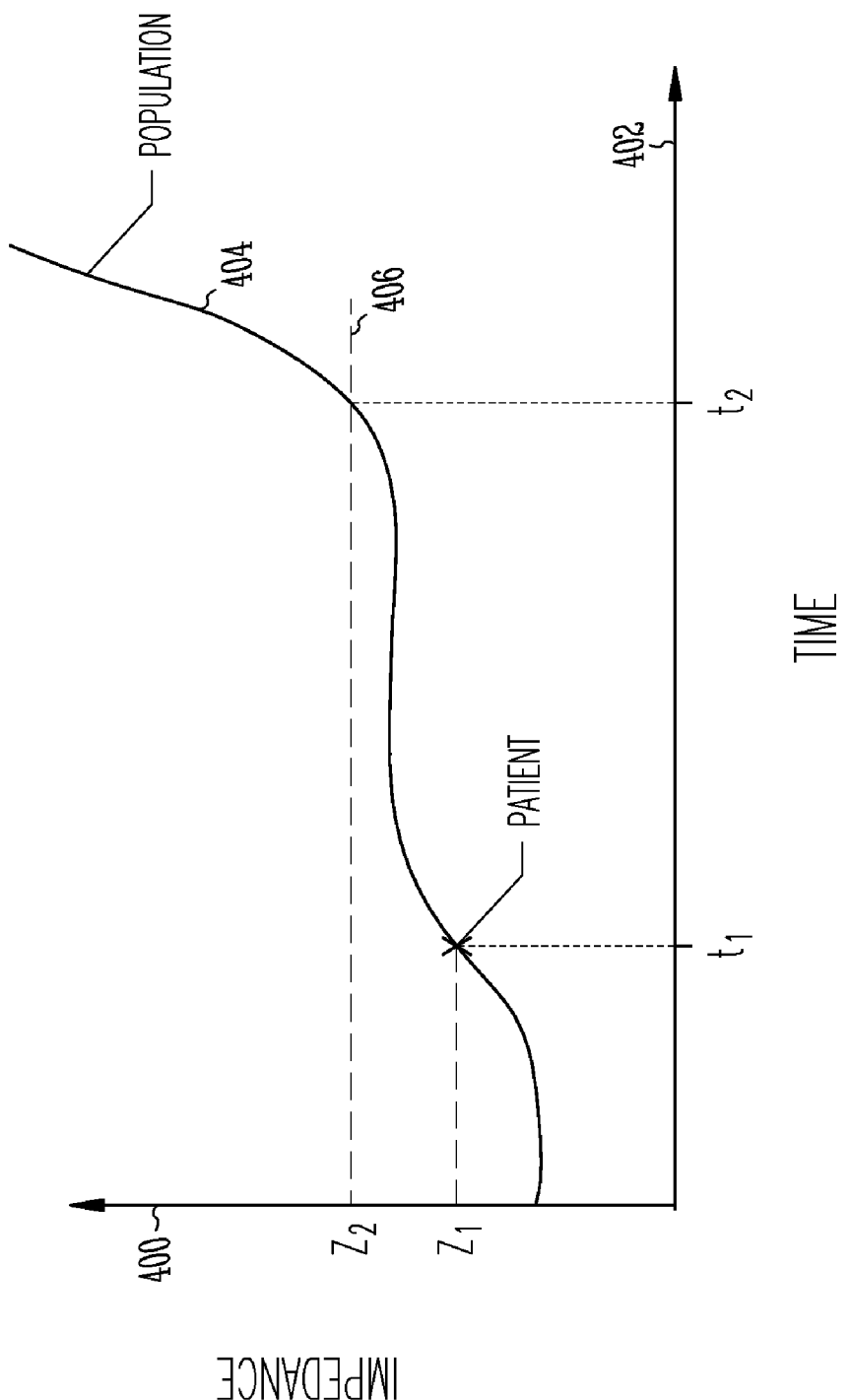
FIG. 4 is a graph of impedance vs. time illustrating generally one conceptualization of how population (or simulation or other predictive) information can be used.

FIG. 4 is a graph of impedance (e.g., axis 400) vs. time (e.g., axis 402) illustrating generally one conceptualization of how population (or simulation or other predictive) information can be used, such as at 308 in FIG. 3, or otherwise. In the example of FIG. 4, population-based impedance data for a particular electrode combination of a particular lead model is aggregated into population impedance data 404. In this conceptualization, lead impedance is initially stable over time, then increases to a plateau, and then abruptly increases beyond a failure threshold 406. In comparing an individual patient to the population data, an individual patient's location on the population curve 404 can be located. If such location indicates impending failure, a corresponding alert can be issued to the patient, caregiver, manufacturer, regulatory agency, or another. If such location indicates that the patient is an "outlier" on the population curve 404, a corresponding alert can be issued to the patient, caregiver, manufacturer, regulatory agency or another.

Moreover, as seen in the illustrative example of FIG. 4, a predicted time-to-failure, $t_2 - t_1$, can be computed. Such information can be provided, for example, to a physician to help the physician schedule an appointment to replace the lead before the predicted failure time, if desired. Moreover, as additional data is acquired from various patients, the threshold 406 can be adjusted in response, either automatically, or upon intervention by a human failure analysis engineer.

Furthermore, a patient's predicted future change in electrode impedance can be used to adjust one or more device parameters of the patient's cardiac rhythm management device, either automatically, or using caregiver control. For example, pacing energy can be automatically increased, depolarization sensing sensitivity can be automatically increased. Similarly, if caregiver control is to be used, a recommendation of device parameter setting changes can be automatically provided to the caregiver to alert and perform triage for the caregiver.

Figure 5:
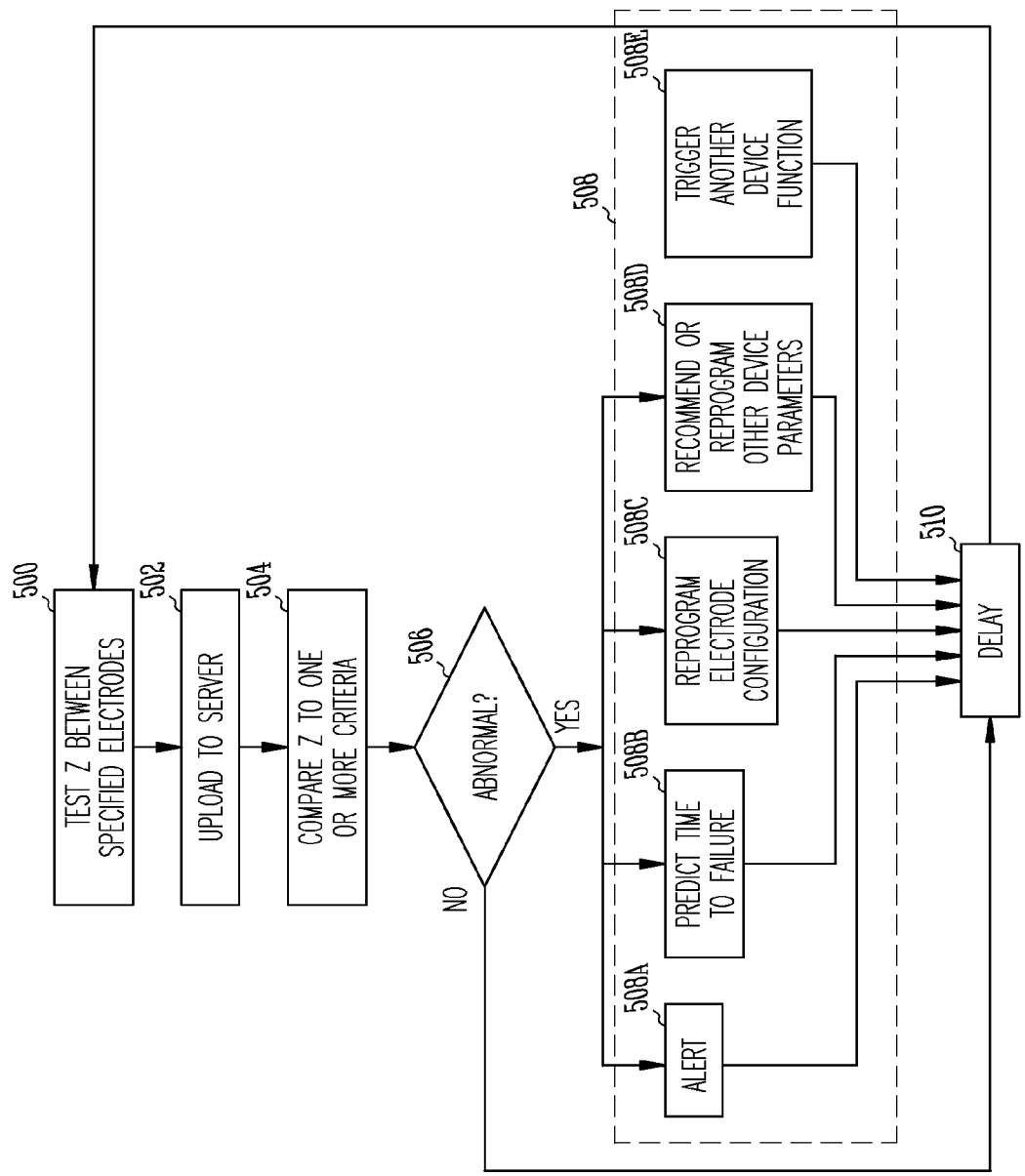
FIG. 5 is a flow chart illustrating examples of various responses to determining that a particular interelectrode impedance measurement is abnormal, such as by comparison to population data, or otherwise.

FIG. 5 is a flow chart illustrating examples of various responses to determining that a particular interelectrode impedance measurement is abnormal, such as by comparison to population data, previous patient data, or otherwise. In this example, at 500, impedance is tested between specified electrodes. At 502, such information is uploaded to the server 204. At 504, the information is compared to one or more criteria, such as to a simple impedance threshold value or band, or to population or predicted (e.g., computer-simulated) impedance data, which may represent one or more failure modes. If, at 506, the a particular interelectrode impedance is deemed abnormal, then at 508, a responsive act is carried out, such as delivering an alert at 508A, predicting and communicating a time-to-failure at 508B, reprogramming or recommending a different electrode configuration at 508C, reprogramming or recommending one or more other changed device parameters (e.g., increase pacing energy, increase depolarization detection gain, etc.) at 508D, or triggering another device feature (e.g., trigger an automatic pacing threshold test to ensure proper pacing energy is being delivered) at 508E. Process flow returns to 500, after any desired delay 510.

Figure 6:
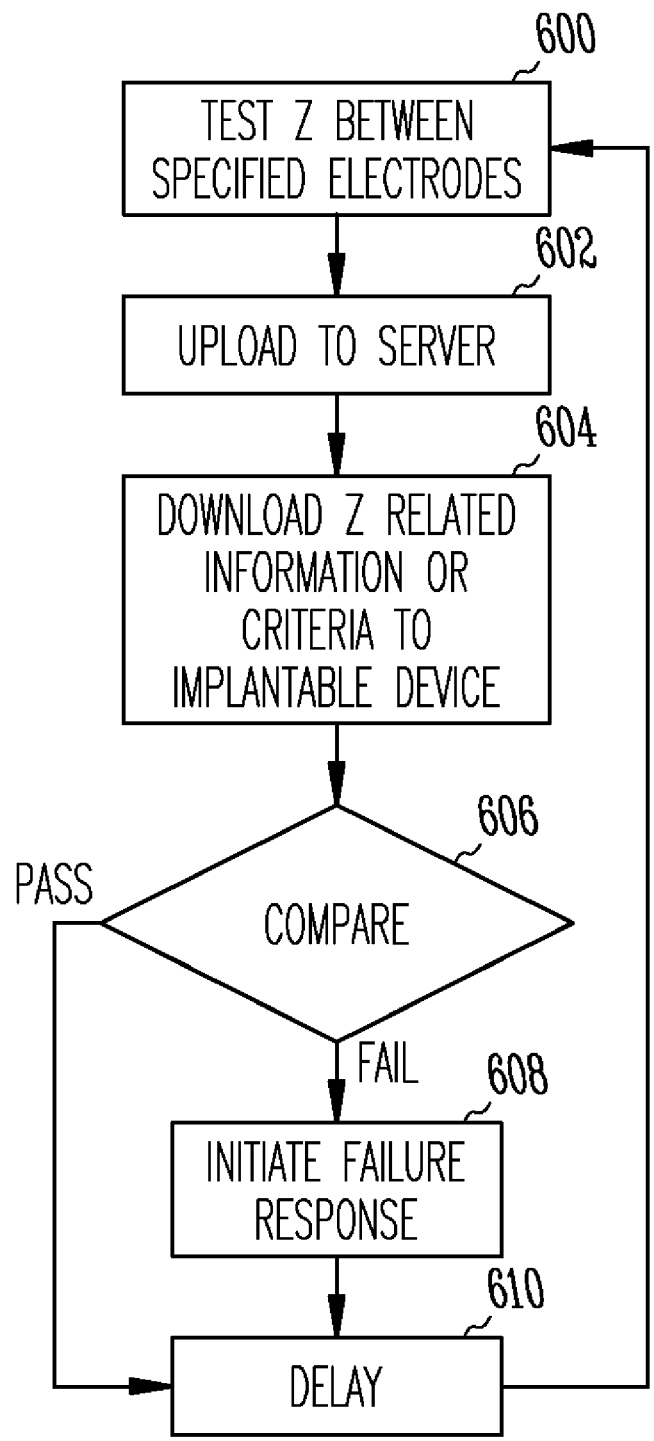
FIG. 6 is a flow chart illustrating an example that is similar to FIGS. 3 and 5, but in which certain functions are performed within the implantable device.

FIG. 6 is a flow chart illustrating an example that is similar to FIGS. 3 and 5, but in which certain functions are performed within the implantable device 100, rather than in the remote server 204. In this example, at 600, the implantable device 100 tests impedance or other characteristics between specified combinations of electrodes, such as discussed above. At 602, resulting information is optionally uploaded to the remote server 204, such as for storing the device history, by itself, or as part of population data, or both. At 604, the remote server 204 downloads impedance related information to the implantable device 100. This may include, for example, criteria against which the measured impedance is to be compared to detect an actual or impending failure. It may include, for example, information by which to predict a time-to-failure. It may include, for example, information about which responsive action to take in the event of an actual or impending lead failure. The information may be based on population-derived data, the particular implantable device's own historical data, simulated or predicted data, or the like.

At 606, the impedance or one or more other characteristics is compared to one or more criteria, such as to determine whether there is an actual or impending lead failure. If a particular electrode configuration fails such a test, then at 608 a failure response is initiated, such as issuing an alert, predicting a time to failure, reprogramming an electrode configuration, recommending or reprogramming one or more other device parameters (e.g., pacing energy), triggering another device function (e.g., a pacing threshold test), or the like. Otherwise, after an optional delay at 610, process flow returns to 600. Although FIG. 6 illustrates a particular example of task division between the implantable device 100 and the remote server 204, other allocations will also be suitable. In general, the remote server 204 advantageously permits population-based data to be used for a particular device, since the remote server 204 will typically communicate with and obtain information from multiple implantable devices 100 in various patients.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. For example, reciting first, second, third, fourth, fifth, and sixth electrodes in a claim does not mean that there must be six electrodes.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A method comprising:
   measuring an electrode impedance for a combination of two or more electrodes connected to an implantable cardiac function management device;
   comparing the measured electrode impedance to a set of population data, the population data including electrode impedances for similar electrode combinations used in various patients in a patient population;
   determining, based on the comparison of the measured electrode impedance to the set of population data, whether the measured electrode impedance represents a significant change for the combination of two or more electrodes; and
   determining, if the measured electrode impedance represents a significant change, a reconfiguration option for the implantable cardiac function management device.

2. The method of claim 1, wherein the set of population data includes predictive laboratory or simulation modeled data when data from electrode impedances for similar electrode combinations used in various patients in a patient population is unavailable or otherwise insufficient.

3. The method of claim 1, wherein the set of population data includes predictive laboratory or simulation modeled data for similar electrode combinations.

4. The method of claim 1, further including creating a population trend over time from the set of population data; and
   wherein determining whether the measured electrode impedance represents a significant change includes determining where the measured electrode impedance falls within the population data trend over time.

5. The method of claim 4, wherein determining where the measured electrode impedance falls within the population data trend over time indicates a predicted time-to-failure for at least one of the two or more electrodes.

6. The method of claim 5, wherein determining the reconfiguration option includes adjusting one or more implantable cardiac function management device parameters based on the predicted time-to-failure for at least one of the two or more electrodes.

7. The method of claim 1, wherein the set of population data includes data from implantable cardiac function devices that exhibited a similar failure mode.

8. The method of claim 1, wherein comparing the measured electrode impedance to the set of population data includes normalizing the measured electrode impedance to compare a change in impedance to the set of population data.

9. The method of claim 1, wherein determining the reconfiguration option includes selecting an alternative electrode to replace one of the two or more electrodes.

10. The method of claim 9, wherein selecting an alternative electrode includes selecting the alternative electrode from an ordered list of electrodes.

11. The method of claim 9, wherein selecting an alternative electrode includes selecting the alternative electrode based on a measured electrode impedance between the alternative electrode and one or more other electrodes.

12. An implantable cardiac function management device comprising,
a processor;
a memory communicatively coupled to the processor, the memory including instructions, which when executed by the processor cause the implantable cardiac function management device to:
measure an electrode impedance for a combination of two or more electrodes connected to the implantable cardiac function management device;
compare the measured electrode impedance to a set of population data, the set of population data including electrode impedances for similar electrode combinations used in various patients in a patient population;
determine, based on the comparison of the measured electrode impedance to the set of population data, whether the measured electrode impedance represents a significant change for the combination of two or more electrodes; and
determine, if the measured electrode impedance represents a significant change, a reconfiguration option for the implantable cardiac function management device.

13. The implantable cardiac function management device of claim 12, wherein the set of population data includes predictive laboratory or simulation modeled data for similar electrode combinations when data from electrode impedances for similar electrode combinations used in various patients in a patient population is unavailable or otherwise insufficient.

14. The implantable cardiac function management device of claim 12, further including instructions which when executed cause the device to:
create a population trend over time from the set of population data; and
wherein instructions to determine whether the measured electrode impedance represents a significant change include instructions to determine where the measured electrode impedance falls within the population data trend over time.

15. The implantable cardiac function management device of claim 14, wherein instructions to determine where the measured electrode impedance falls within the population data trend over time include instructions to create a predicted time-to-failure for at least one of the two or more electrodes.

16. The implantable cardiac function management device of claim 15, wherein instructions to determine the reconfiguration option include instructions to adjust one or more implantable cardiac function management device parameters based on the predicted time-to-failure for at least one of the two or more electrodes.

17. The implantable cardiac function management device of claim 12, wherein the set of population data includes data from implantable cardiac function devices that exhibited a similar failure mode.

18. The implantable cardiac function management device of claim 12, wherein instructions to compare the measured electrode impedance to the set of population data include instructions to normalize the measured electrode impedance to compare a change in impedance to the set of population data.

19. The implantable cardiac function management device of claim 12, wherein instructions to determine the reconfiguration option include instructions to select an alternative electrode to replace one of the two or more electrodes.

* * * * *